United States Patent
Herrmann et al.

(10) Patent No.: US 9,027,477 B2
(45) Date of Patent: May 12, 2015

(54) WRINKLE DETECTION IN CONTINUOUS FEED PRINTERS

(71) Applicant: Xerox Corporation, Norwalk, CT (US)

(72) Inventors: Douglas K. Herrmann, Webster, NY (US); Jason M. LeFevre, Penfield, NY (US); Derek A. Bryl, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 132 days.

(21) Appl. No.: 13/852,096

(22) Filed: Mar. 28, 2013

(65) Prior Publication Data

US 2014/0290519 A1     Oct. 2, 2014

(51) Int. Cl.
| | |
|---|---|
| B41F 33/00 | (2006.01) |
| B41F 3/08 | (2006.01) |
| B41F 21/12 | (2006.01) |
| B41F 21/00 | (2006.01) |

(52) U.S. Cl.
CPC ...................................... B41F 21/00 (2013.01)

(58) Field of Classification Search
CPC ............ B41J 11/46; G03G 2215/0161; G03G 15/6582; G03G 15/6573
USPC ..................... 101/481–485; 400/76
See application file for complete search history.

(56) References Cited

U.S. PATENT DOCUMENTS

| | | | |
|---|---|---|---|
| 4,184,770 A | 1/1980 | Pinior | |
| 4,428,287 A * | 1/1984 | Greiner | 101/170 |
| 4,851,696 A | 7/1989 | West | |
| 5,949,550 A | 9/1999 | Arndt et al. | |
| 5,992,973 A * | 11/1999 | Wen | 347/43 |
| 8,256,345 B2 | 9/2012 | Denninger et al. | |
| 2011/0042437 A1 | 2/2011 | Sugie et al. | |
| 2011/0243636 A1* | 10/2011 | Viturro et al. | 400/583 |

* cited by examiner

*Primary Examiner* — Blake A Tankersley
*Assistant Examiner* — Marissa Ferguson Samreth
(74) *Attorney, Agent, or Firm* — Maginot, Moore & Beck, LLP

(57) ABSTRACT

A web printing system automatically detects the location of a wrinkle in a moving web. The web has a plurality of marked reference positions including an inboard position, a center position, and an outboard position. A plurality of contact image sensors detect the reference positions after the web passes through a spreader and an inboard distance and an outboard distance are respectively measured from the center position. If the inboard distance is less than a nominal inboard distance, the wrinkle is identified as inboard of the center position. If the outboard distance is less than a nominal outboard distance, the wrinkle is identified as outboard of the center position. The machine operator is notified of the fault condition and takes action to remedy the situation.

8 Claims, 6 Drawing Sheets

WRINKLE DETECTION IN CONTINUOUS FEED PRINTERS

TECHNICAL FIELD

The device and method disclosed in this document relate to printers generally and, more particularly, to systems and methods for detecting wrinkles in continuous feed media inkjet printers.

BACKGROUND

Ink jet printers have printheads that operate a plurality of inkjets that eject liquid ink onto an image receiving surface. The ink can be stored in reservoirs positioned within the printer. Such ink can be aqueous, oil, solvent-based, or UV curable ink or an ink emulsion. Other inkjet printers receive ink in a solid form and then melt the solid ink to generate liquid ink for ejection onto the image receiving surface. In these solid ink printers, the solid ink can be in the form of pellets, ink sticks, granules or other shapes. Typically, an ink loader delivers solid ink pellets or ink sticks placed in the ink loader through a feed chute or channel to a melting device. A reservoir receives the melted ink and supplies the melted ink to one or more printheads. Other inkjet printers use gel ink. Gel inks are also heated to a predetermined temperature to alter the viscosity of the ink so the ink is suitable for ejection by a printhead.

A typical full width inkjet printer uses one or more printheads. Each printhead typically contains an array of individual nozzles for ejecting drops of ink across an open gap to an image receiving surface to form an image. The image receiving surface can be the surface of a continuous web of recording media, the surfaces of a series of media sheets, or the surface of an image receiving member, such as a rotating print drum or endless belt. Images printed on a rotating surface are later transferred and fixed to recording media by mechanical force in a transfix nip formed by the rotating surface and a transfix roller.

In an inkjet printhead, individual piezoelectric, thermal, or acoustic actuators generate mechanical forces that eject ink from an ink filled pressure chamber and through an orifice in response to an electrical voltage signal, sometimes called a firing signal. The amplitude, frequency, or duration of the firing signals affects the amount of ink ejected in each drop. The firing signal is generated by a printhead controller in accordance with image data. An inkjet printer forms a printed image in accordance with the image data by printing a pattern of individual ink drops at particular locations on the image receiving member. The locations where the ink drops land are sometimes called "ink drop locations," "ink drop positions," or "pixels." Thus, a printing operation can be viewed as the placement of ink drops on an image receiving member in accordance with image data.

When printing on a continuous web or recording media, a spreading device is typically used to spread and fix the ink drops once they are placed on the media. The spreading device can include a high-load pressure roller configured with a conformable covering and an adjacent image side roller configured with a solid, non-conformable surface that interact to form a high-force nip into which the media is fed. The spreading and fixing of the ink on the media enables the printing operation to achieve a desired image quality and permanence. Occasionally, a wrinkle can form in the media web if the high-load pressure roller is out of alignment with the image side roller, or if the loading of the nip is not appropriate for the media weight, width or edge-registration position. In existing inkjet printers, an operator periodically inspects the condition of the web to visually detect whether a wrinkle is present. Once a wrinkle is detected, the operator implements a maintenance procedure to eliminate the wrinkle. Consequently, the operator may not detect the wrinkle until its severity passes an unacceptable threshold. Moreover, even after the wrinkle is detected, the operator must further determine if the wrinkle is inboard or outboard of the center of the web so that the pressure roller can be adjusted accordingly. Therefore, automated detection of the presence and position of a wrinkle in moving web is desirable to minimize machine downtime and material waste arising from continued printing while a wrinkle condition exists.

SUMMARY

A method for identifying a position of a wrinkle in continuous feed media has been developed. The method includes identifying a first distance in a cross-process direction on a web moving in a process direction, the first distance being identified with reference to a center position of the web and a first position of the web, identifying a second distance in a cross-process direction on the web, the second distance being identified with reference to the center position of the web and a second position on the web, the first position and the second position being different, and identifying a position of a wrinkle in the web with reference to a difference between the first distance and a first predetermined distance or a difference between the second distance and to a second predetermined distance.

A web printing system has been developed to implement a method for identifying a position of a wrinkle in continuous feed media. The system includes a media transport system configured to move a media web through the web printing system in a process direction, the web having a first position, a center position, and a second position marked across the web in a cross-process direction perpendicular to the process direction, an optical sensor configured to generate image data corresponding to the first position, the center position, and the second position, and a controller operatively connected to the media transport system and the optical sensor, the controller configured to operate the media transport system to move the web through the web printing system, operate the optical sensor to general image data that corresponds to the first position, the center position, and the second position, identify a first distance in the cross-process direction on the web with reference to the center position and the first position, identify a second distance in the cross-process direction on the web with reference to the center position and the second position, the first position and the second position being different, measure a first difference between the first distance and a first predetermined distance and a second difference between the second distance and a second predetermined distance, and identify a position of a wrinkle in the web with reference to the first difference and the second difference.

BRIEF DESCRIPTION OF THE DRAWINGS

The foregoing aspects and other features of the system and method for identifying a position of a wrinkle in continuous feed media are explained in the following description, taken in connection with the accompanying drawings.

DETAILED DESCRIPTION

Figure 1:
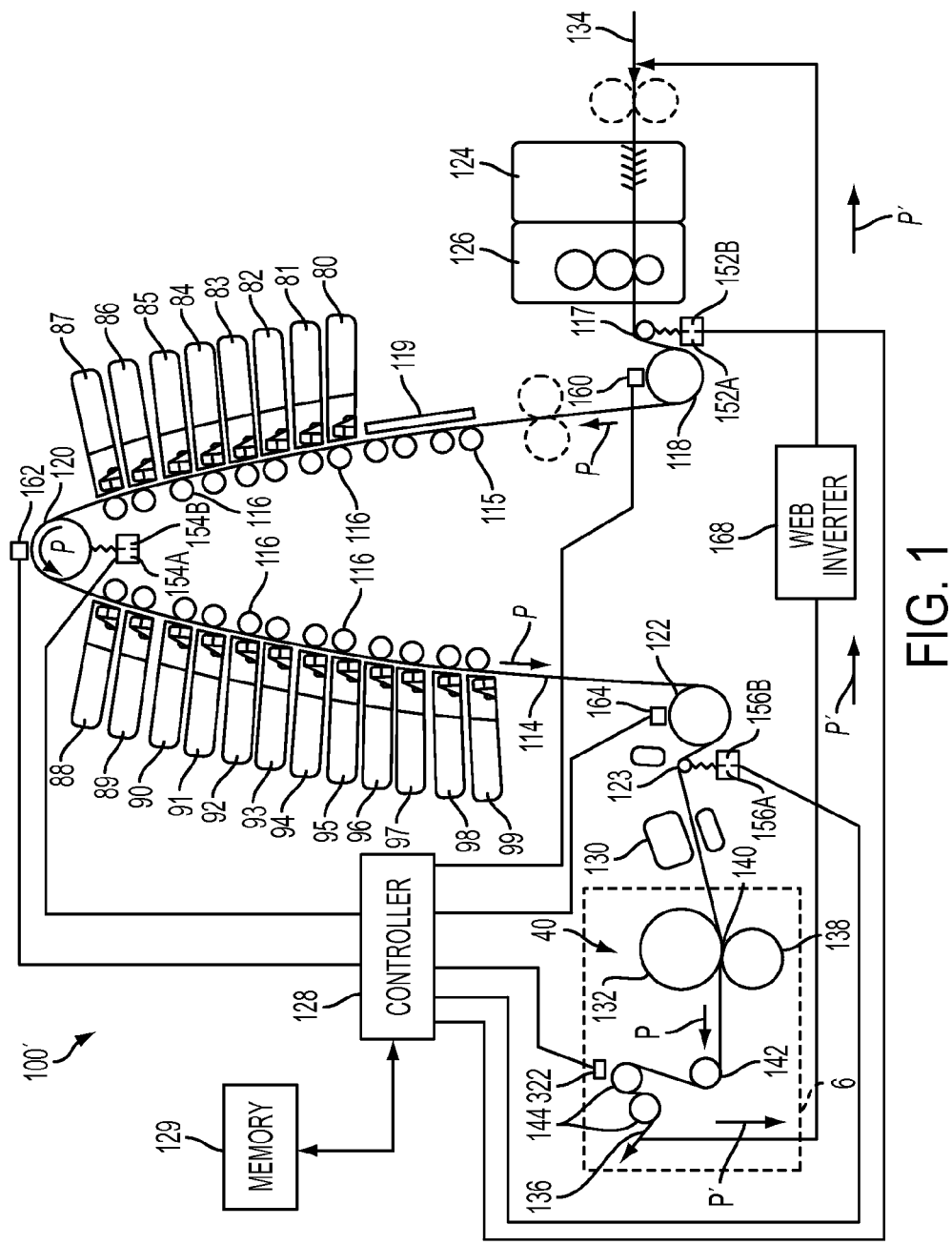
FIG. 1 is a schematic view of a prior art inkjet printer modified to implement a method for identifying a position of a wrinkle in a media web used therein.

For a general understanding of the environment for the device and method disclosed herein as well as the details for the device and method, reference is made to the drawings. In the drawings, like reference numerals designate like elements. As used herein, the word "printer" encompasses any apparatus that produces images with colorants on media, such as digital copiers, bookmaking machines, facsimile machines, multi-function machines, and the like. As used herein, the term "process direction" refers to a direction of movement of a print medium, such as a continuous media web pulled from a roll of paper or other suitable print medium along a media path through a printer. The print medium moves past one or more printheads in a print zone within the printer to receive ink images and then pass other printer components, such as heaters, fusers, pressure rollers, and on-sheet imaging sensors, that are arranged along the media path. As used herein, the term "cross-process" direction refers to an axis that is perpendicular to the process direction along the surface of the print medium.

Figure 8:
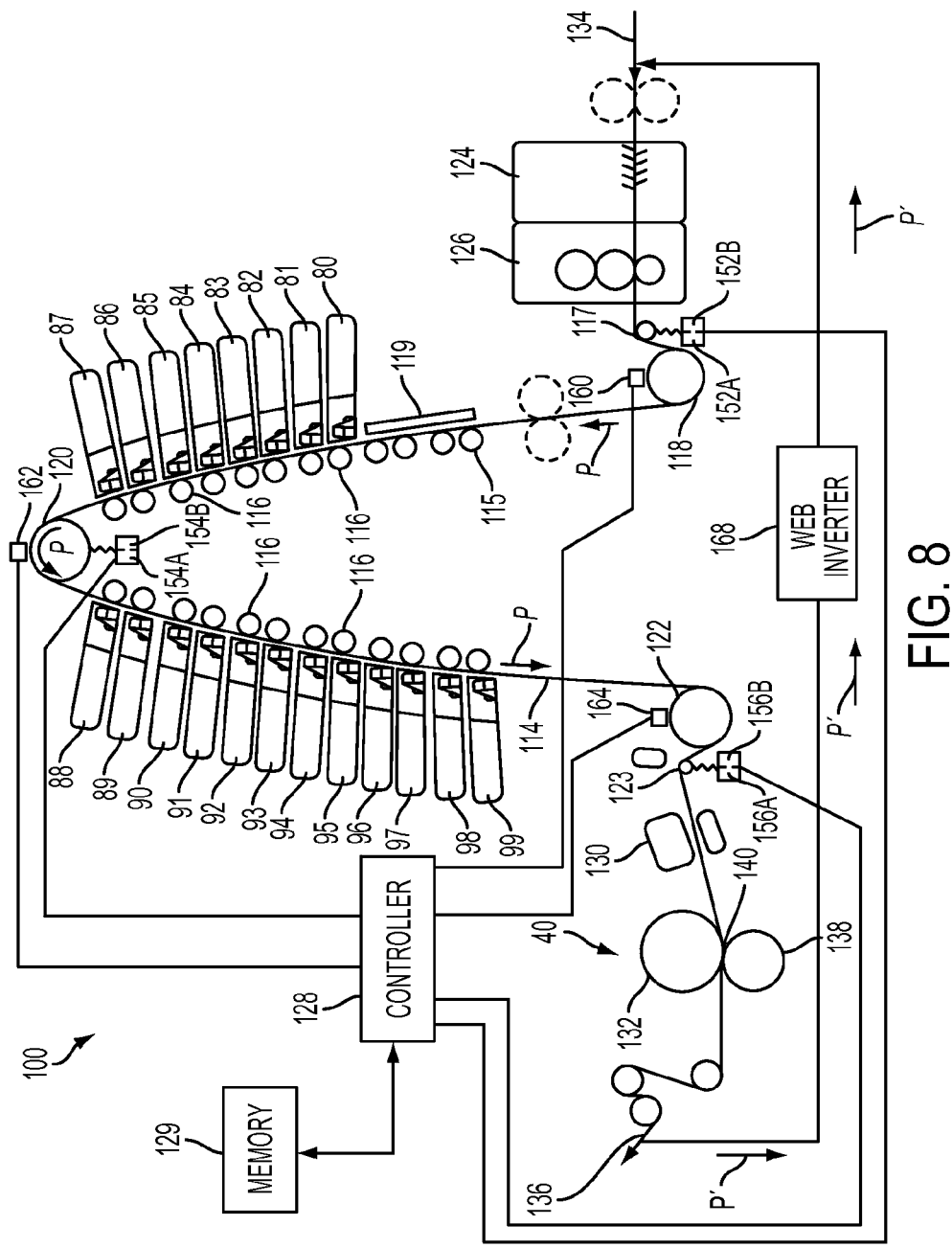
FIG. 8 is a schematic view of a prior art inkjet printer that ejects ink onto a continuous web of media as the media moves past the printheads in the system.

FIG. 8 depicts a prior art inkjet printer 100 having elements pertinent to the present disclosure. An inkjet printer, for the purposes of this disclosure, employs one or more inkjet printheads to eject drops of ink onto a surface of an image receiving member, such as paper, another print medium, or an indirect member, such as a rotating image drum or belt. Although a system and method for identifying a position of a wrinkle in a web are described below with reference to the printer 100 depicted in FIG. 8, which uses phase change ink, the subject system and method disclosed herein can be used in printers that use other forms of ink, such as aqueous ink, or that eject ink onto a series of media sheets.

The printer 100 is configured to print ink images with a "phase-change ink," by which is meant an ink that is substantially solid at room temperature and that transitions to a liquid state when heated to a phase change ink melting temperature for ejecting onto the imaging receiving member surface. The phase change ink melting temperature is any temperature that is capable of melting solid phase change ink into liquid or molten form. In one embodiment, the phase change ink melting temperature is approximately 70° C. to 140° C. In alternative embodiments, the ink utilized in the printer comprises UV curable gel ink. Gel inks are also heated before being ejected by the inkjet ejectors of the printhead. As used herein, liquid ink refers to melted solid ink, heated gel ink, or other known forms of ink, such as aqueous inks, ink emulsions, ink suspensions, ink solutions, or the like.

The printer 100 is an example of a direct-to-web, continuous-media, phase-change inkjet printer. As shown in FIG. 8, the printer 100 includes twenty print modules 80-99, a controller 128, a memory 129, backer roller 115, backer rollers 116, pre-heater roller 118, apex roller 120, leveler roller 122, tension sensors 152A-152B, 154A-154B, and 156A-156B, and velocity sensors, such as encoders 160, 162, and 164. The print modules 80-99 are positioned sequentially along a media path P and form a print zone from a first print module 80 to a last print module 99 for forming images on a print medium 114 as the print medium 114 travels past the print modules. Each print module 80-83 provides a magenta ink. Each print module 84-87 provides cyan ink. Each print module 88-91 provides yellow ink. Each print module 92-95 provides black ink. Each print module 96-99 provides a clear ink as a finish coat. In all other respects, the print modules 80-99 are substantially identical.

The media web 114 travels through the media path P guided by rollers 115 and 116, pre-heater roller 118, apex roller 120, and leveler roller 122. A heated plate 119 is provided along the path adjacent roller 115. In FIG. 8, the apex roller 120 is an "idler" roller, meaning that the roller rotates in response to engaging the moving media web 114, but is otherwise uncoupled from any motors or other drive mechanisms in the printing system 100. The pre-heater roller 118, apex roller 120, and leveler roller 122 are each examples of a capstan roller that engages the media web 114 on a portion of its surface. A brush cleaner 124 and a contact roller 126 are located at one end of the media path P.

Following the print zone along the media path P are one or more "mid-heaters" 130. A mid-heater 130 can use contact, radiant, conductive, and/or convective heat to control the temperature of the media. The mid-heater 130 brings the ink placed on the media web 114 to a temperature suitable for desired properties when the ink on the media web 114 is sent through a fixing assembly 40. In one embodiment, a useful range for a target temperature for the media exiting the mid-heater is about 35° C. to about 80° C. The leveler roller 122 has the effect of equalizing the ink and substrate temperatures to within about 15° C. of each other. Lower ink temperature gives less line spread while higher ink temperature causes show-through (visibility of the image from the other side of the print). The mid-heater 30 adjusts substrate and ink temperatures to 0° C. to 20° C. above the temperature of the fixing assembly 40.

Following the mid-heaters 130, the fixing assembly 40 applies heat and/or pressure to the media web 114 to fix the images to the media web 114. The fixing assembly 40 includes any suitable device or apparatus for fixing images to the media including heated or unheated pressure rollers, radiant heaters, heat lamps, and the like. In the embodiment of FIG. 8, the fixing assembly includes a "spreader" 40, which applies a predetermined pressure, and in some implementations, heat, to the media web 114. The function of the spreader 40 is to flatten the individual ink droplets, strings of ink droplets, or lines of ink on media web 114 and flatten the ink with pressure and, in some systems, heat. The spreader 40 flattens the ink drops to fill spaces between adjacent drops and form uniform images on the media web 114. In addition to spreading the ink, the spreader 40 improves fixation of the ink image to the media web 114 by increasing ink layer cohesion and/or increasing the ink-web adhesion. The spreader 40 includes rollers, such as image-side roller 132 and pressure roller 138, to apply heat and pressure to the media web 114 in a nip 140 formed between the rollers. Either roller can include heat elements to bring the media web 114 to a temperature in a range from about 35° C. to about 80° C. In alternative embodiments, the fixing assembly spreads the ink using non-contact heating (without pressure) of the media web 114 after the print zone. Such a non-contact fixing assembly can use any suitable type of heater to heat the media web 114 to a desired temperature, such as a radiant heater, UV heating lamps, and the like.

The spreader 40 can include a cleaning/oiling station (not shown) associated with image-side roller 132. The station cleans and/or applies a layer of release agent or other material to the roller surface. The release agent material can be an amino silicone oil having viscosity of about 10-200 centipoises. A small amount of oil transfers from the station to the media web 114, with the printer 100 transferring approximately 1-10 mg per A4 sheet-sized portion of the media web 114. In one embodiment, the mid-heater 130 and spreader 40 are combined into a single unit with their respective functions occurring relative to the same portion of the media web 114 simultaneously. In another embodiment, the media web 114 is maintained at a high temperature as the media web 114 exits the print zone to enable spreading of the ink.

A web inverter 168 is configured to direct the media web 114 from the end 136 of media path to the beginning 134 of the media path through an inverter path P'. The web inverter 168 flips the media web 114 and the inverter path P' returns the flipped web to the inlet 134 to enable single-engine ("Mobius") duplex printing in which the print modules 80-99 form one or more ink images on a second side (second side ink image) of the media web 114 after forming one or more images on the first side (first side ink image). In this operating mode, a first section of the media web 114 moves through the media path P in tandem with a second section of the media web, with the first section receiving ink images on the first side of the media web and the second section receiving ink images on the second side. Each of the print modules 80-99 is configured to eject ink drops onto both sections of the media web 114. Each of the rollers 115, 116, 118, 120, and 122 also engage both the first and second sections of the media web. After the second side of the media web 114 is imaged, the media web 114 passes the end of the media path 136. The registration of a second side ink image to a first side ink image forms a duplex image. In another embodiment, one print module is configured to span the width of the recording media, such that two print modules located side by side are used to eject ink on the first and second sections of the web.

Each of the print modules 80-99 includes an array of printheads that are arranged across the width of both the first section of media web 114 and the second section of the media web 114. Ink ejectors in each printhead in the array of printheads are configured to eject ink drops onto predetermined locations of both the first and second sections of the media web 114.

Operation and control of the various subsystems, components and functions of printing system 100 are performed with the aid of a controller 128 and memory 129. In particular, the controller 128 monitors the velocity and tension of the media web 114 and determines timing of ink drop ejection from the print modules 80-99. The controller 128 can be implemented with general or specialized programmable processors that execute programmed instructions. The controller 128 is operatively connected to the memory 129 to enable the controller 128 to read instructions and to read and write data required to perform the programmed functions in the memory 129. The memory 129 can also hold one or more values that identify tension levels for operating the printing system with at least one type of print medium used for the media web 114. These components can be provided on a printed circuit card or provided as a circuit in an application specific integrated circuit (ASIC). Each of the circuits can be implemented with a separate processor or multiple circuits can be implemented on the same processor. Alternatively, the circuits can be implemented with discrete components or circuits provided in VLSI circuits. Also, the circuits described herein can be implemented with a combination of processors, ASICs, discrete components, or VLSI circuits.

The encoders 160, 162, and 164 are operatively connected to the preheater roller 118, apex roller 120, and leveler roller 122, respectively. Each of the encoders 160, 162, and 164 are velocity sensors that generate an angular velocity signal corresponding to an angular velocity of a respective one of the rollers 120, 118, and 122. Typical embodiments of the encoders 160, 162, and 164 include Hall effect sensors configured to generate signals in response to the movement of magnets operatively connected to the rollers and optical wheel encoders that generate signals in response to a periodic interruption to a light beam as a corresponding roller rotates. The controller 128 is operatively connected to the encoders 160, 162, and 164 to receive the angular velocity signals. The controller 128 can include hardware circuits, software routines, or both, configured to identify a linear velocity of each of the rollers 120, 118, and 122 using the generated signals and a known radius for each roller.

The tension sensors 152A-152B, 154A-154B, and 156A-156B are operatively connected to a guide roller 117, apex roller 120, and post-leveler roller 123, respectively. The guide roller 117 is positioned on the media path P prior to the preheater roller 118. The post-leveler roller 123 is positioned on the media path P after the leveler roller 122. Each tension sensor generates a signal corresponding to the tension force applied to the media web 114 at the position of the corresponding roller. Each tension sensor can be a load cell configured to generate a signal that corresponds to the mechanical tension force between the media web 114 and the corresponding roller.

In FIG. 8 where two sections of the media web 114 engage each roller in tandem, each of the tension sensors are paired to identify the tension on each section of the media web 114. In embodiments where one surface of the media web engages each roller, a single tension sensor can be used instead. The tension sensors 152A-152B generate signals corresponding to the tension on the media web 114 as the media web 114 enters the print zone passing the print modules 80-99. The print zone is also known as the ink application zone or the "jetting zone." The tension sensors 154A-154B generate signals corresponding to the tension of the media web 114 around the apex roller 120 at an intermediate position in the print zone. The tension sensors 156A-156B generate signals corresponding to the tension of the media web around leveler roller as the media web 114 exits the print zone. The tension sensors 152A-152B, 154A-154B, and 156A-156B are operatively connected to the controller 128 to enable the controller 128 to receive the generated signals and to monitor the tension between apex roller 118 and the media web 114 during operation.

In solid inkjet (SIJ) printers, such as the printer 100 of FIG. 8, the high pressure applied to the media web 114 in the spreader 40 can cause a wrinkle to form in the web when the printed images are fixed on the web. Although removal of the wrinkle is possible, such removal requires an operator to visually inspect the media web 114 to determine the position of the wrinkle with respect to the center of the web. The operator then adjusts the loading forces on the pressure roller 138 from side-to-side to eliminate the wrinkle. A potential issue with this approach to removing the wrinkle is the need for the operator to continuously inspect the web to identify the presence and, if present, the position of the wrinkle. Human error can lead the operator in such a situation to fail to recognize the occurrence of a wrinkle until the defect becomes severe enough in nature to draw the operator's attention to it.

Figure 2:
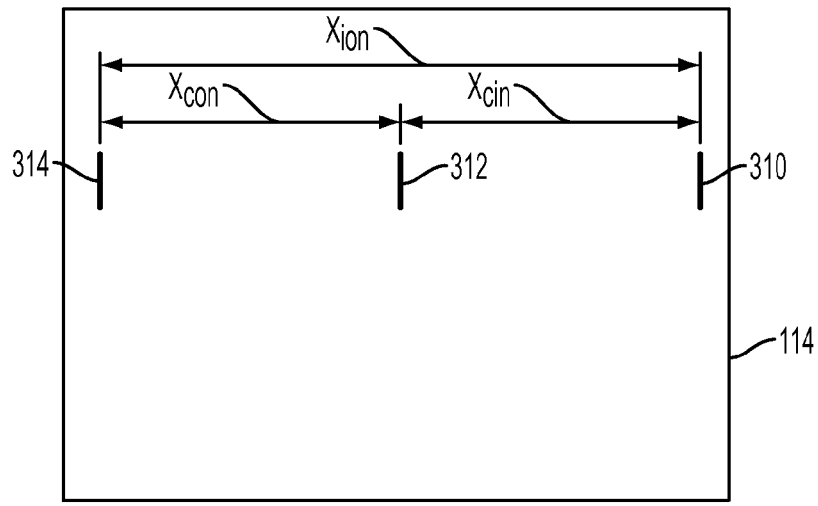
FIG. 2 is a schematic view of the media web of the printer of FIG. 1 having reference positions printed at an inboard position, a center position, and an outboard position across a width of the media web in an inter-document zone.

FIG. 1 shows the prior art printer 100 modified to include a system for identifying the presence and position of a wrinkle in the moving web 114. As best shown in FIG. 2, the media web 114 of the modified printer 100' has positions marked on one or both of its surfaces that identify an inboard position 310, a center position 312, and an outboard position 314 (collectively the "reference positions") across the web 114 in the cross-process direction. In the embodiment shown, at least one printhead is operated to eject ink onto the web 114 to mark the reference positions 310, 312, 314. The reference positions 310, 312, 314 as shown are marked as respective lines each having a length extending in the process direction P. In other embodiments, the reference positions 310, 312, 314 are marked as fiducials or optical character recognition (OCR) marks. As discussed in more detail below, the marks identifying the reference positions 310, 312, 314 can take any form that permits high-speed detection of the marks within a limited scan range.

FIG. 2 shows the nominal locations of the reference positions 310, 312, 314 immediately after the position marks are formed on the web. For purposes of this disclosure, the following subscripts are used in conjunction with the letter X to denote the various position-to-position distances shown in the figures: (ci)=distance between the center position 312 and the inboard position 310, (co)=distance between the center position 312 and the outboard position 314, (io)=distance between the inboard position 310 and the outboard position 314, (n)="nominal" condition of web having no wrinkle between the indicated positions, and (w)="wrinkled" condition of web having at least one wrinkle between the indicated positions. For example, the distance $X_{cin}$ refers to the distance between the center position 312 and the inboard position 310 when the condition of the web 114 is nominal—that is, no wrinkle is present between the center position 312 and the inboard position 310.

The reference positions 310, 312, 314 are initially formed on the web 114 with equal spacing between each position. Since the distances between the inkjets forming the reference positions 310, 312, 314 are known, the distances between each of the reference positions 310, 312, 314 at the time of their formation are also known. As such, the known distance between the center position 312 and the inboard position 310 defines an inboard nominal distance $X_{cin}$ and the known distance between the center position 312 and the outboard position 314 defines an outboard nominal distance $X_{con}$. Similarly, the known distance between the inboard position 310 and the outboard position 314 defines an overall nominal distance $X_{ion}$.

Referring again to FIG. 1, the modified printer 100' includes an optical sensor 322 operatively connected to the controller 128 and configured to generate image data corresponding to the marked reference positions 310, 312, 314. In the embodiment shown, the optical sensor 322 is positioned proximate to an s-wrap roller 144 located downstream of the spreader 40. The positioning of the optical sensor 322 proximate to the s-wrap roller 142 or any other downstream roller of the spreader 40, such as an idler roller 142, provides the optical sensor 322 with a constant distance to the web 114 with no fluctuation in web distance or profile due to edge curl or cockle within the web.

Figure 4:
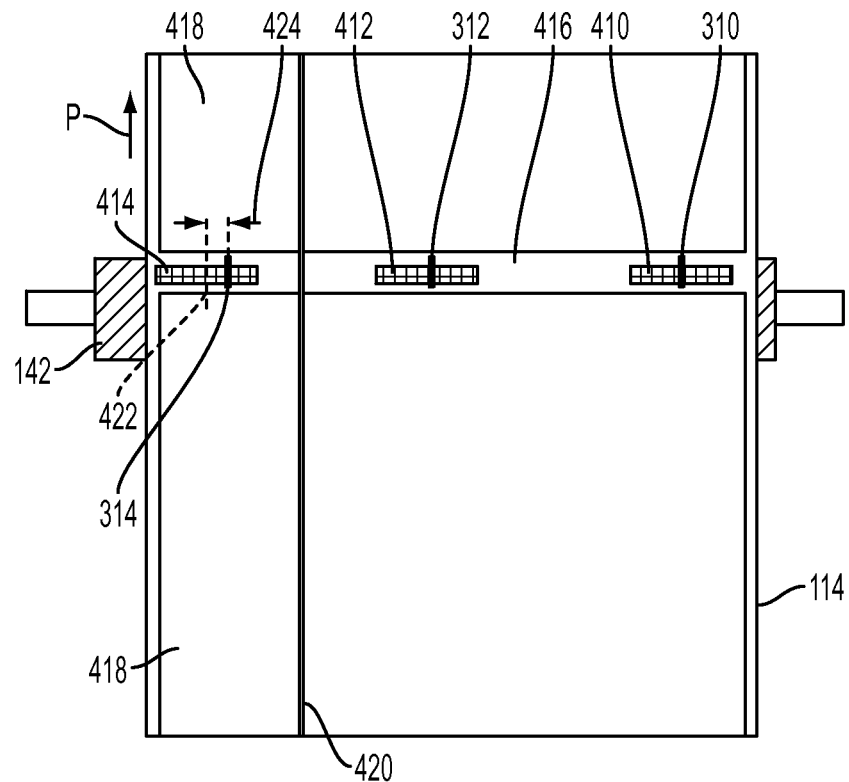

FIG. 4 shows the positioning of the optical sensor 322 with respect to the marked reference positions 310, 312, 314 on the web 114. The optical sensor 322 includes a plurality of contact image sensors positioned to detect the marked reference positions 310, 312, 314. In the embodiment shown, an inboard sensor 410 is positioned to detect the marked inboard position 310, a center sensor 412 is positioned to detect the marked center position 312, and an outboard sensor 414 is positioned to detect the marked outboard position 314. The contact image sensors 410, 412, 414 are positioned such that each reference position moves past an approximate midpoint of its associated sensor when the distances between the reference positions are nominal $X_{cin}$, $X_{con}$, $X_{ion}$. The known distances between the contact image sensors 410, 412, 414 are then calibrated as part of a setup procedure.

The reference positions 310, 312, 314 shown in FIG. 4 are marked in an inter-document area 416 located between image areas 418. In one embodiment, the reference positions 310, 312, 314 are marked at each consecutive inter-document area 416 along web 114 in the process direction P. In another embodiment, the reference positions 310, 312, 314 are marked at every other inter-document area 416 along the web 114 in the process direction P. In yet another embodiment, the reference positions 310, 312, 314 are intermittently marked as part of a manual or automatic maintenance procedure.

The use of discrete printed marks to identify the reference positions 310, 312, 314 allows for the use of shorter-length contact image sensors—meaning the sensors are shorter in the cross-process direction—since it is not necessary to scan the entire web width. For example, the modified printer 100' depicted in FIG. 1 can implement an A8 (50 mm) length sensor to detect each of the printed marks in the inter-document area 416. In one practical embodiment, the modified printer 100' implements the Lite-On® DL115 A8 54.2 mm 600 dpi, 2 ms/line CMOS sensor to detect the printed marks in the inter-document area 416. With a maximum web speed of the modified printer 100' of 500 ft/min, a one-inch mark passes through the inter-document area 416 in 10 ms, allowing the Lite-On® DL115 sensor multiple reads per mark. The length of the mark in this embodiment is based on the inter-document area 416 between the image areas 418 being approximately 25.4 mm in the process direction P.

Figure 3:
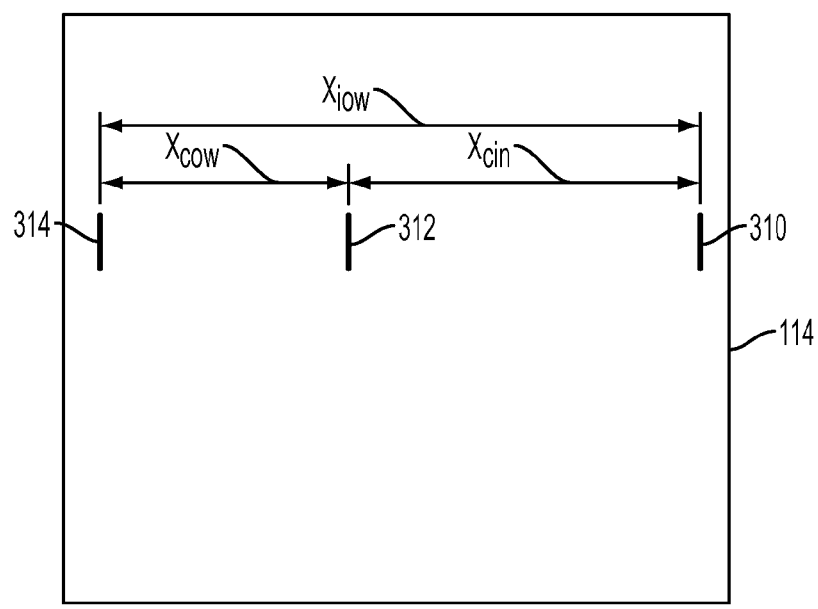
FIGS. 3-5 are schematic views illustrating how the formation of the wrinkle in the media web causes the locations of the marked reference positions to change with respect to each other and with respect to a plurality of contact image sensors.
Figure 5:
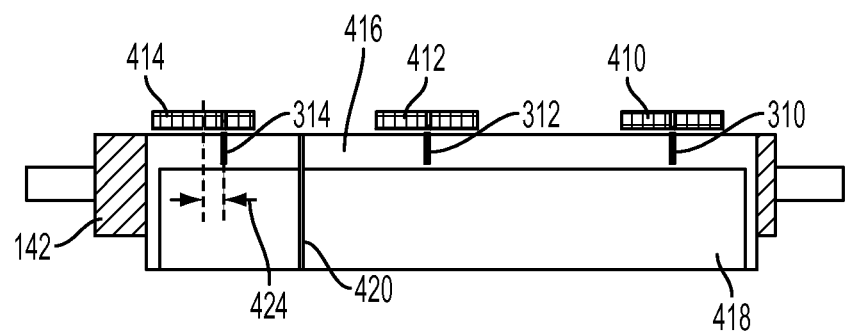

FIGS. 3-5 illustrate how the formation of a wrinkle 420 in the web 114 causes the locations of the marked reference positions 310, 312, 314 to change with respect to each other and with respect to the contact image sensors 410, 412, 414. In the embodiment shown in the figures, the wrinkle 420 is formed between the center position 312 and the outboard position 314. As shown by comparing FIG. 2 and FIG. 3, the distance between the center position 312 and the outboard position 314 is reduced because a portion of the width of the web is folded or creased in the cross-process direction to form the wrinkle 420. As such, the reduced distance between the center position 312 and the outboard position 314 due to the wrinkle 420 represents an outboard wrinkle distance $X_{cow}$ that is less than the outboard nominal distance $X_{con}$. The distance between the center position 312 and the inboard distance 310 remains the inboard nominal distance $X_{cin}$ because the wrinkle 420 does not affect the width of the web between these positions. The distance between the inboard position 310 and the outboard position 314 is also reduced due to the wrinkle and represents an overall wrinkle distance $X_{iow}$ that is less than the overall nominal distance $X_{ion}$.

Although not shown in the figures, if the wrinkle 420 forms between the center position 312 and the inboard position 310, the distance between these positions is reduced and represents an inboard wrinkle distance $X_{ciw}$ that is less than the inboard nominal distance $X_{cin}$. The distance between center position 312 and the outboard position 314 remains the outboard nominal distance $X_{con}$ because the wrinkle 420 does not affect the width of the web between these positions. The distance between the inboard position 310 and the outboard position 314 is reduced due to the wrinkle and represents the overall wrinkle distance $X_{iow}$.

Referring now to FIG. 4 and FIG. 5, the calibrated positioning of the contact image sensors 410, 412, 414 enables each of the sensors to detect if its corresponding marked reference position 310, 312, 314 is shifted from a target position 422. If the reference position 310, 312, 314 is shifted from its target position, the image data generated by the sensor enables the controller 128 to calculate a distance off target 424 for that shifted position. For example, in the embodiment shown in the figures, the formation of the wrinkle 420 between the center position 312 and the outboard position 314 causes the marked outboard position 314 to shift toward the center position 312. The distance off target 424 for this position is the distance between the detected location of the marked outboard position and its target position 422.

Figure 6:
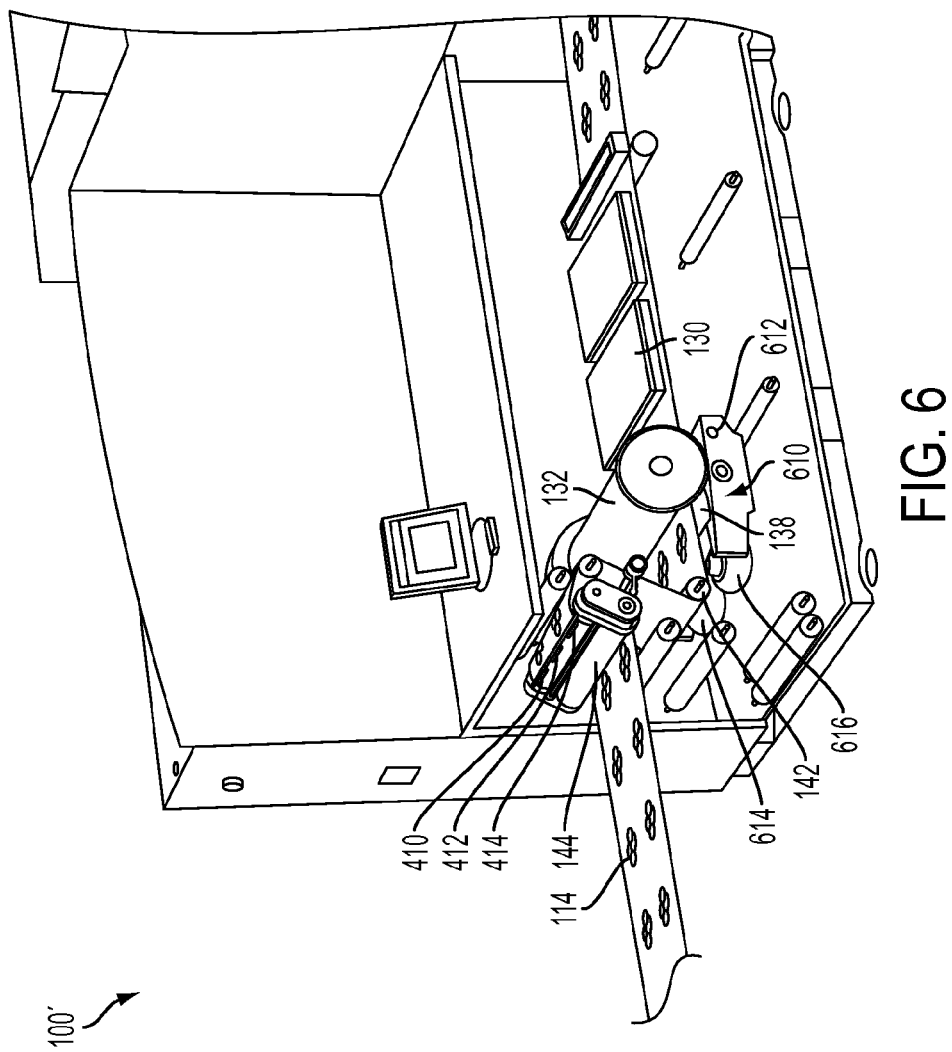
FIG. 6 is an enlarged perspective view of a spreader associated with the modified printer of FIG. 1.

FIG. 6 shows an enlarged perspective view of the spreader 40 of the modified printer 100' of FIG. 1. In the embodiment shown in FIG. 6, the pressure roller 138 is attached to a pressure assembly 610 that is rotatable about a pivot 612. The rotation of the pressure assembly 610 about the pivot 612 adjusts the relative position of the pressure roller 138 with respect to the image side roller 132 to increase or decrease the pressure in the nip 140. The pressure assembly 610 includes an actuator to cause the pressure assembly 610 and the attached pressure roller 138 to rotate towards or away from the image side roller 132. In the embodiment shown, the actuator includes an inboard airbag 614 and an outboard airbag 616 that are independently inflatable and deflatable against a surface to adjust the force of the pressure roller 138 across image side roller 132. In one embodiment, an operator actuates manual pumps to inflate or deflate the airbags 614, 616 to adjust the nip pressure. In another embodiment, the controller 128 operates one or more electro-pneumatic air regulators to inflate or deflate the airbags 614, 616.

If the web is wrinkling on either the inboard edge or the outboard edge, that edge of the nip needs to rotate faster. To make one edge move faster relative to the center of the nip, the operator applies more load to the edge that is wrinkling. For example, in one practical embodiment in which the inboard edge is wrinkling, the operator inflates the inboard airbag 614 to increase the load at the inboard edge in 10 kgf increments until the wrinkle is eliminated. If the wrinkle is occurring at the outboard edge, the operator inflates the outboard airbag 616 to increase the load at the outboard edge until the wrinkle is eliminated. If increasing the load does not eliminate the wrinkle and the respective airbag 614, 616 is applying its maximum force on the edge (NVM=567 kg), the load on the opposite airbag 614, 614 is decreased in 10 kgf increments until the wrinkle is eliminated. The system disclosed herein enables automatic detection of the presence of a wrinkle within the web 114 and further identifies the position of the wrinkle with respect to the center of the web to enable an operator to adjust the nip pressure as needed to eliminate the wrinkle.

Figure 7:
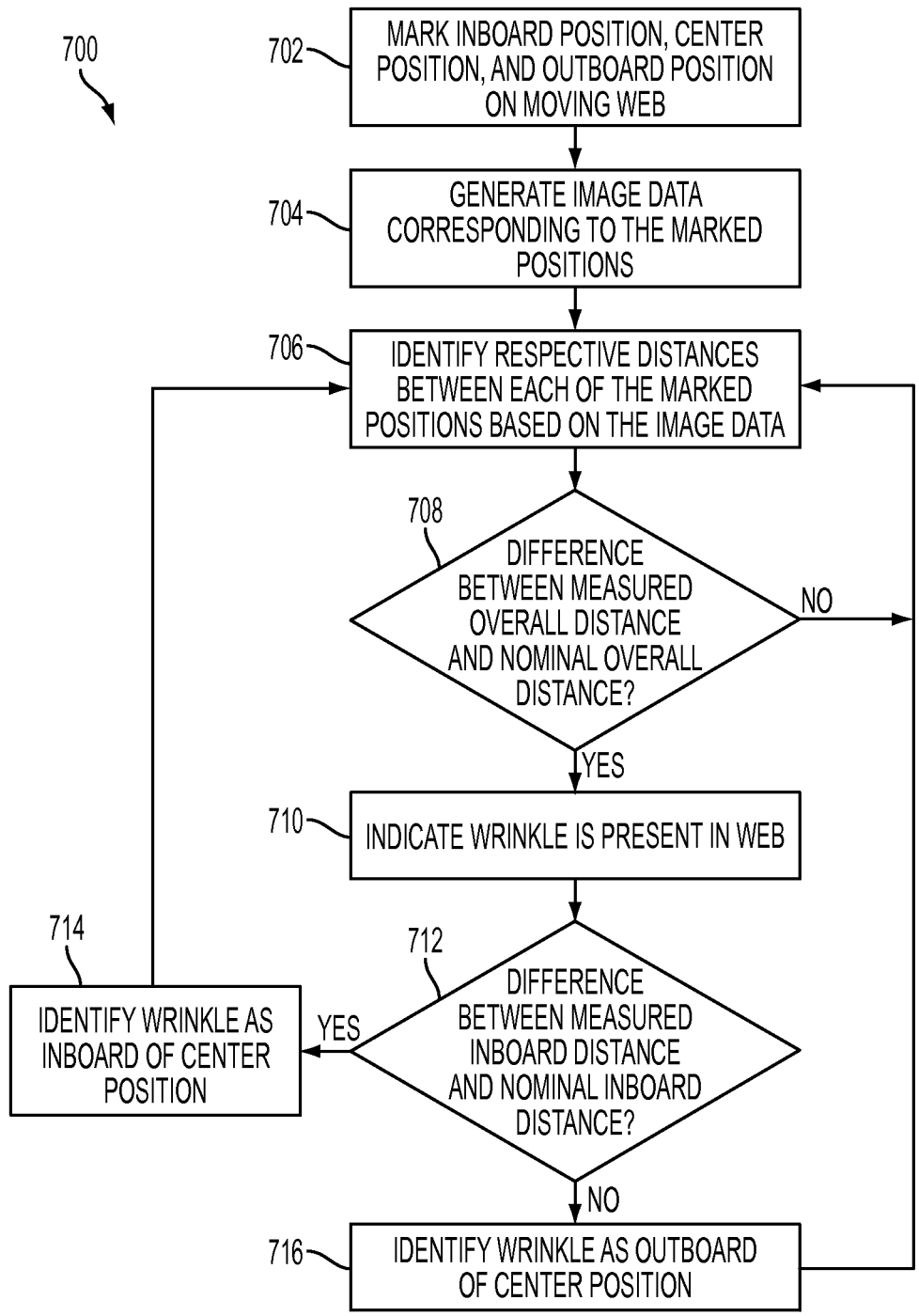
FIG. 7 is a flow diagram of a process for identifying the position of the wrinkle in the media web of the printer of FIG. 1.

A flow diagram of a process 700 for identifying the position of a wrinkle in a moving web is shown in FIG. 7. The controller is configured to execute programmed instructions stored in a memory operatively connected to the controller to implement the process 700. In the discussion below, a reference to the process performing a function or action refers to the controller executing programmed instructions stored in the memory to operate one or more components to perform the function or action. The process 700 is described with reference to the modified printer 100' shown in FIGS. 1-6.

The process 700 begins by operating at least one printhead to eject ink onto the moving web 114 to mark an inboard position 310, a center position 312, and an outboard position (collectively the "reference positions") (block 702). As used herein, the term "center position" refers to the approximate midpoint or center of the web in the cross-process direction. As used herein, the terms "inboard position" or "rear edge" and the terms "outboard position" or "front edge" refer to discrete positions spaced from the center position that approximate the respective side edges of the web.

After the reference positions 310, 312, 314 are marked (block 702), the contact image sensors 410, 412, 414 are operated to generate image data that correspond to the reference positions 310, 312, 314 (block 704). In one embodiment, the contact image sensors 410, 412, 414 operate continuously to generate image data for each set of marked reference positions 310, 312, 314 printed on the web 114. In another embodiment, top of form (TOF) marks located on the web 114 trigger the contact image sensors 410, 412, 414 to detect selected sets of the marked reference positions 310, 312, 314.

The controller 128 executing programmed instructions stored in a memory operatively connected to the controller processes the generated image data to identify (i) an inboard distance $X_{ci}$ measured between the center position 312 and the inboard position 310, (ii) an outboard distance $X_{co}$ measured between the center position 312 and the outboard position 314, and (iii) an overall distance $X_{io}$ measured between the inboard position 310 and the outboard position 314 (block 706). Once the overall distance $X_{io}$ is identified (block 706), the controller 128 determines if there is a difference between the overall distance $X_{io}$ and the overall nominal distance $X_{ion}$ (block 708). If no difference exists between the overall distance $X_{io}$ and the overall nominal distance $X_{ion}$, the process 700 returns to the processing described with reference to block 706 and continues to identify respective inboard $X_{ci}$, outboard $X_{co}$, and overall $X_{io}$ distances for a new set of marked reference positions. If a difference between the overall distance $X_{io}$ and the overall nominal distance $X_{ion}$ exists and the overall distance $X_{io}$ is less than the overall nominal distance $X_{ion}$, the controller 128 causes one or more devices associated with the printer 100' to indicate the presence of a wrinkle (block 710). In one embodiment, the controller operates an I/O device associated with the printer to notify an operator of the wrinkle. In another embodiment, the controller operates an audio device to signal the presence of the wrinkle.

If a wrinkle is detected in the web (blocks 708 and 710), the process 700 continues by determining the position of the wrinkle relative to the center position 312. For example, in the embodiment of the process 700 shown in FIG. 7, the controller 128 determines if a difference between the inboard distance $X_{ci}$ and the inboard nominal distance $X_{cin}$ exists (block 712). If a difference between the inboard distance $X_{ci}$ and the inboard nominal distance $X_{cin}$ exists and the inboard distance $X_{ci}$ is less than the inboard nominal distance $X_{cin}$, the controller 128 identifies the wrinkle as inboard of the center position 312 (block 714). If no difference exists between the inboard distance $X_{ci}$ and the inboard nominal distance $X_{cin}$, the controller 128 identifies the wrinkle as outboard of the center position 312 (block 716). After the wrinkle has been identified as either inboard (block 714) or outboard (block 716) of the center position 312, the process returns to the processing described above with reference to block 706 and continues to identify respective inboard $X_{ci}$, outboard $X_{co}$, and overall $X_{io}$ distances for a new set of marked reference positions.

In another embodiment, the difference between the outboard distance $X_{co}$ and the outboard nominal distance $X_{ion}$ is determined in the processing described with reference to block 712. In this embodiment, if a difference between the outboard distance $X_{co}$ and the outboard nominal distance $X_{con}$ exists and the outboard distance $X_{co}$ is less than the outboard nominal distance $X_{con}$, the controller 128 identifies the wrinkle as outboard of the center position 312 in Block 714. If no difference exists between the outboard distance $X_{co}$ and the outboard nominal distance $X_{con}$, the controller 128 identifies the wrinkle as inboard of the center position 312 in Block 716. Also in this embodiment, after the wrinkle has been identified as either outboard (block 714) or inboard (block 716) of the center position 312, the process returns to the processing described with reference to block 706 and continues to identify respective inboard $X_{ci}$, outboard $X_{co}$, and overall $X_{io}$ distances for a new set of marked reference positions. As discussed above with reference to FIG. 6, either the operator or the controller 128 can adjust the position of pressure roller 138 to eliminate the wrinkle once the position of the wrinkle is identified by the process 700.

It will be appreciated that variants of the above-disclosed and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following claims.

What is claimed:

1. A web printing system comprising:
   a media transport system configured to move a media web through the web printing system in a process direction;
   at least one printhead having a plurality of inkjets extending in a cross-process direction across a width of the media web, the cross-process direction being perpendicular to the process direction in a plane of the media web, the printhead configured to eject ink drops from the plurality of inkjets onto the media web as the media web moves in the process direction;
   a plurality of contact image sensors positioned to detect a first position marked on the media web, a center position marked on the media web, and a second position marked on the media web; and
   a controller operatively connected to the media transport system, the at least one printhead and the plurality of contact image sensors, the controller configured to:
   operate the media transport system to move the media web through the web printing system;
   operate the at least one printhead to eject ink onto the media web as the media web moves through the web printing system in the process direction to mark a first position, a center position, and a second position onto the media web with the first position marked on the media web and the second position marked on the media web being equally spaced from the center position marked on the media web in the cross-process direction;
   operate the plurality of contact image sensors to generate image data that corresponds to the first position marked on the media web, the center position marked on the media web, and the second position marked on the media web;
   identify a first distance in the cross-process direction on the media web with reference to the image data corresponding to the center position and the image data corresponding to the first position;
   identify a second distance in the cross-process direction on the media web with reference to the image data corresponding to the center position and the image data corresponding to the second position, the image data corresponding to the first position and the image data corresponding to the second position being different;
   measure a first difference between the first distance and a first predetermined distance and a second difference between the second distance and a second predetermined distance; and
   identify a position of a wrinkle in the media web as being inboard of the center position marked on the media web in response to the first distance being less than the first predetermined distance, and identify the position of the wrinkle as outboard of the center position marked on the media web in response to the second distance being less than the second predetermined distance.

2. The web printing system of claim 1, the plurality of contact image sensors further comprising:
   a first contact image sensor positioned to detect the first position marked on the media web;
   a second contact image sensor positioned to detect the center position marked on the media web; and
   a third contact image sensor positioned to detect the second position marked on the media web.

3. The web printing system of claim 1, further comprising:
   a spreader roller and a pressure roller with which the spreader roller forms a nip, the nip configured to apply pressure to the media web as the media web is moved through the nip, the controller being further configured to:
   prompt an operator to adjust a loading of the pressure roller against the spreader roller in response to the identified position of the wrinkle in the media web.

4. The web printing system of claim 1, the controller being further configured to:
   operate the at least one printhead to mark the first position on the media web, the center position on the media web, and the second position on the media web in an interdocument area of the media web as the media web moves through the web printing system.

5. A web printing system comprising:
   a media transport system configured to move a media web through the web printing system in a process direction;
   at least one printhead having a plurality of inkjets extending in a cross-process direction across a width of the media web, the cross-process direction being perpendicular to the process direction in a plane of the media web, the printhead configured to eject ink drops from the plurality of inkjets onto the media web as the media web moves in the process direction;
   a plurality of contact image sensors positioned to detect a first position marked on the media web, a center position marked on the media web, and a second position marked on the media web; and
   a controller operatively connected to the media transport system, the at least one printhead and the plurality of contact image sensors, the controller configured to:
   operate the media transport system to move the media web through the web printing system;
   operate the at least one printhead to eject ink onto the media web as the media web moves through the web printing system in the process direction to mark a first position, a center position, and a second position onto the media web with the first position marked on the media web and the second position marked on the media web being equally spaced from the center position marked on the media web in the cross-process direction;

operate the plurality of contact image sensors to generate image data that corresponds to the first position marked on the media web, the center position marked on the media web, and the second position marked on the media web;

identify continuously a first distance in the cross-process direction on the media web with reference to the image data corresponding to the center position and the image data corresponding to the first position;

identify continuously a second distance in the cross-process direction on the media web with reference to the image data corresponding to the center position and the image data corresponding to the second position, the image data corresponding to the first position and the image data corresponding to the second position being different and the identification of the first distance and the second distance being in response to the plurality of contact image sensors detecting at least one top of form (TOF) mark on the media web;

measure a first difference between the first distance and a first predetermined distance and a second difference between the second distance and a second predetermined distance; and identify a position of a wrinkle in the media web with reference to the first difference and the second difference.

6. The web printing system of claim 5, the plurality of contact image sensors further comprising:
a first contact image sensor positioned to detect the first position marked on the media web;
a second contact image sensor positioned to detect the center position marked on the media web; and
a third contact image sensor positioned to detect the second position marked on the media web.

7. The web printing system of claim 5, further comprising:
a spreader roller and a pressure roller with which the spreader roller forms a nip, the nip configured to apply pressure to the media web as the media web is moved through the nip, the controller being further configured to:
prompt an operator to adjust a loading of the pressure roller against the spreader roller in response to the identified position of the wrinkle in the media web.

8. The web printing system of claim 5, the controller being further configured to:
operate the at least one printhead to mark the first position on the media web, the center position on the media web, and the second position on the media web in an inter-document area of the media web as the media web moves through the web printing system.

* * * * *